(12) United States Patent
Fauver et al.

(10) Patent No.: US 6,991,738 B1
(45) Date of Patent: Jan. 31, 2006

(54) FLOW-THROUGH DRUM CENTRIFUGE

(75) Inventors: Mark E. Fauver, Seattle, WA (US); Alan C. Nelson, Gig Harbor, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/964,513

(22) Filed: Oct. 13, 2004

(51) Int. Cl.
*B01D 21/26* (2006.01)
*B01D 37/02* (2006.01)

(52) U.S. Cl. .............. 210/771; 210/778; 210/780; 210/787; 210/791; 210/360.1; 210/380.1; 210/393; 210/396; 210/402; 118/55; 118/58; 422/72; 494/37; 494/43; 494/58

(58) Field of Classification Search .............. 210/770, 210/778, 780, 802, 783, 787, 803, 360.1, 210/393, 394, 396, 402, 771, 791, 380.1; 118/55, 58; 422/72, 101; 427/2.1, 2.13; 494/36, 37, 43, 58
See application file for complete search history.

(56) References Cited

U.S. PATENT DOCUMENTS

| | | | |
|---|---|---|---|
| 2,883,054 A * | 4/1959 | Sanchez | ..................... 210/394 |
| 3,470,373 A | 9/1969 | Brewer | |
| 3,497,690 A | 2/1970 | Wheeless, Jr. | |
| 3,598,471 A | 8/1971 | Baldwin | |
| 3,657,537 A | 4/1972 | Wheeless, Jr. | |
| 3,748,468 A | 7/1973 | Hartman | |
| 3,833,762 A | 9/1974 | Gudmundsen | |
| 3,960,449 A | 6/1976 | Carlton | |
| 3,999,047 A | 12/1976 | Green | |
| 4,175,860 A | 11/1979 | Bacus | |
| 4,183,623 A | 1/1980 | Haines | |
| 4,200,353 A | 4/1980 | Hoffman | |
| 4,209,827 A | 6/1980 | Duinker | |
| 4,293,221 A | 10/1981 | Kay | |
| 4,360,885 A | 11/1982 | Edgar | |
| 4,422,146 A | 12/1983 | Yamaguchi | |
| 4,657,676 A | 4/1987 | Keary | |
| 4,858,128 A | 8/1989 | Nowak | |
| 4,873,653 A | 10/1989 | Grosskopf | |
| 4,891,829 A | 1/1990 | Deckman | |
| 4,966,576 A | 10/1990 | Schulz | |
| 5,141,609 A | 8/1992 | Sweedler et al. | |
| 5,148,502 A | 9/1992 | Tsujiuchi et al. | |
| 5,236,604 A * | 8/1993 | Fiehler | ..................... 210/787 |
| 5,281,517 A | 1/1994 | Bacus et al. | |

(Continued)

FOREIGN PATENT DOCUMENTS

WO    WO 02/095476 A2    11/2002

OTHER PUBLICATIONS

Kikuchi, S. et al., "Three-dimensional computed tomography for optical microscopes," Optics Communications 107 (1994) 432-444.

(Continued)

*Primary Examiner*—David A. Reifsnyder
(74) *Attorney, Agent, or Firm*—George A. Leone (57) ABSTRACT

A process includes coating a cylinder having an inner wall and a cylinder axis with a gel coating on the inner wall. Then a specimen mixture including solvent is made to flow through the cylinder while the cylinder is being continuously rotated. The specimen mixture is initially directed to flow along the cylinder axis and such that specimen particles from the specimen mixture are accelerated off the cylinder axis toward the inner wall, so as to form a film of specimen particles embedded into the gel coating.

17 Claims, 9 Drawing Sheets

U.S. PATENT DOCUMENTS

| | | | |
|---|---|---|---|
| 5,308,990 | A | 5/1994 | Takahashi et al. |
| 5,312,535 | A | 5/1994 | Waska et al. |
| 5,321,501 | A | 6/1994 | Swanson et al. |
| 5,421,330 | A | 6/1995 | Thirion |
| 5,630,938 | A | 5/1997 | Feller |
| 5,668,887 | A | 9/1997 | Parker et al. |
| 5,676,631 | A | 10/1997 | Kunz |
| 5,680,484 | A | 10/1997 | Ohyama et al. |
| 5,681,483 | A * | 10/1997 | Navaree et al. ............. 210/787 |
| 5,710,429 | A | 1/1998 | Alfano et al. |
| 5,739,540 | A | 4/1998 | Motomura |
| 5,741,411 | A | 4/1998 | Yeung et al. |
| 5,760,901 | A | 6/1998 | Hill |
| 5,760,951 | A | 6/1998 | Dixon et al. |
| 5,828,408 | A | 10/1998 | Mottin et al. |
| 5,848,123 | A | 12/1998 | Strommer |
| 5,878,103 | A | 3/1999 | Sauer et al. |
| 5,880,838 | A | 3/1999 | Marx et al. |
| 5,909,476 | A | 6/1999 | Cheng et al. |
| 5,915,048 | A | 6/1999 | Hill et al. |
| 5,987,158 | A | 11/1999 | Meyer |
| 6,005,617 | A | 12/1999 | Shimamoto et al. |
| 6,026,174 | A | 2/2000 | Palcic |
| 6,038,067 | A | 3/2000 | George |
| 6,047,080 | A | 4/2000 | Chen et al. |
| 6,072,624 | A | 6/2000 | Dixon et al. |
| 6,091,983 | A | 7/2000 | Alfano et al. |
| 6,130,958 | A | 10/2000 | Rohler et al. |
| 6,165,734 | A | 12/2000 | Garini |
| 6,201,628 | B1 | 3/2001 | Basiji |
| 6,211,955 | B1 | 4/2001 | Basiji |
| 6,215,587 | B1 | 4/2001 | Alfano et al. |
| 6,248,988 | B1 | 6/2001 | Krantz |
| 6,249,341 | B1 | 6/2001 | Basiji |
| 6,251,586 | B1 | 6/2001 | Mulshine |
| 6,251,615 | B1 | 6/2001 | Oberhardt |
| 6,252,979 | B1 | 6/2001 | Lee |
| 6,312,914 | B1 | 11/2001 | Kardos et al. |
| 6,388,809 | B1 | 5/2002 | MacAulay |
| 6,452,179 | B1 | 9/2002 | Coates et al. |
| 6,519,355 | B2 | 2/2003 | Nelson |
| 6,529,614 | B1 | 3/2003 | Chao et al. |
| 6,591,003 | B2 | 7/2003 | Chu |
| 6,636,623 | B2 | 10/2003 | Nelson |
| 6,697,508 | B2 | 2/2004 | Nelson |
| 6,741,730 | B2 | 5/2004 | Rahn |
| 6,755,969 | B2 | 6/2004 | Kirker |
| 6,770,893 | B2 | 8/2004 | Nelson |
| 2001/0012069 | A1 | 8/2001 | Derndinger et al. |
| 2002/0045525 | A1 | 4/2002 | Marziali |
| 2002/0141625 | A1 | 10/2002 | Nelson |
| 2002/0161534 | A1 | 10/2002 | Adler et al. |
| 2002/0173034 | A1 | 11/2002 | Barbera-Guillem |
| 2003/0199758 | A1 | 10/2003 | Nelson |
| 2004/0001618 | A1 | 1/2004 | Rahn |
| 2004/0076319 | A1 | 4/2004 | Fauver |

OTHER PUBLICATIONS

Kikuchi, S. et al., "Three-dimensional microscopic computed tomography based on general Radon transform for optical imaging systems," Optics Communications 123 (1996).

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-382, 1987.

Gilbert, P, "Iterative Methods for the Three dimensional Reconstruction of an Object from Projections," Journal of Theoretical Biology 36pp. 105-117, 1972.

Oppenheim, BE, More Accurate Algorithms for Iterative 3 dimensional Reconstruction, IEEE Transactions on Nuclear Science NS-21pp. 72-77, 1974.

Singer, JR, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32pp. 205-216, 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947-1957,1989, #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frquency-domain Near-infrared Photo Diffusion Imaging: Initial Evaluation in Multitarget Tissuelike Phantoms", Medical Physics 25(2)pp. 183-193, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, 3$^{rd}$ ed., Wiley-Liss, 1995.

HJ Tiziani and MI Uhde, Three-dimensional analysis by a microlens array confocal arrangements (*Applied Optics* 33, 567 [1994]).

Bayat, S, Le Duc, G, Porra, L, Berrruyer, G. Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282 (R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-14, 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney, JH and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," SCIENCE, vol. 296, pp. 541-545, Apr. 19, 2002.

Sharpe, J, review, "Optical Projection Tomography as a New Tool for Studying Embryo Anatomy," *J. Anat.* (2003), pp. 175-181.

RH Anderson, "Close-up imaging of documents and displays with lens arrays," *Applied Optics* 18, 477 (1979).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectra-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements," Cytometry, vol. 2, No. 5, pp. 327-336 (1982).

M. Rozycka, et al., "Optical Diffraction as a Tool for Semiautomatic, Quantitative Analysis of Tissue Specimens, " Cytometry, vol. 2, No. 4, pp. 244-248 (1982).

Almeida and Fuji, Fourier transform differences and averaged simularities in diatoms, Applied Optics, vol. 18, No. 10, pp. 1663-1667, (1979).

Smolinska and Dawidowicz, "Extraction of common or different part from optical images," Institute of Physics, Warsaw Technical Univeristy, 222-223, (undated).

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149-156, 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78: 435-449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504-509.

George, JS et al., "Virtual Pinhole Confocal Microscope," Physics Division Progress Report, www.lanl.gov/p/pdfs/papp_pinhole.pdf, (1999-2000).

Pawley, JB, *Handbook of Biological Confocal Microscopy*, Plenum Press, NY, 479-490 (1995).

* cited by examiner

FLOW-THROUGH DRUM CENTRIFUGE

FIELD OF THE INVENTION

The present invention relates generally to specimen preparation for analysis, and more particularly, to biological specimen preparation for optical tomography.

BACKGROUND OF THE INVENTION

Specimen preparation for pathological analysis for detection of diseases such as cancer often affect specimen characteristics. Therefore, reliable procedures are needed in order to produce quality specimens, especially for analysis by automated devices. During preparation, unwanted contaminants must be removed in the specimen, while maintaining specimen characteristics, such as, for example, morphological details of biological cells.

SUMMARY OF THE INVENTION

The present invention provides a process and apparatus for separation of specimen particles. The process includes coating a cylinder having an inner wall and a cylinder axis with a gel coating on the inner wall. Then a specimen mixture including solvent is made to flow through the cylinder while the cylinder is being continuously rotated, wherein the specimen mixture is initially directed to flow along the cylinder axis and such that specimen particles from the specimen mixture are accelerated off the cylinder axis toward the inner wall, so as to form a film of specimen particles embedded into the gel coating.

DETAILED DESCRIPTION OF THE PREFERRED EMBODIMENTS

The invention is described herein with respect to specific examples relating to biological cells. However, it will be understood that the examples are for the purpose of illustrating the principals of the invention, and that the invention is not so limited.

Figure 1:
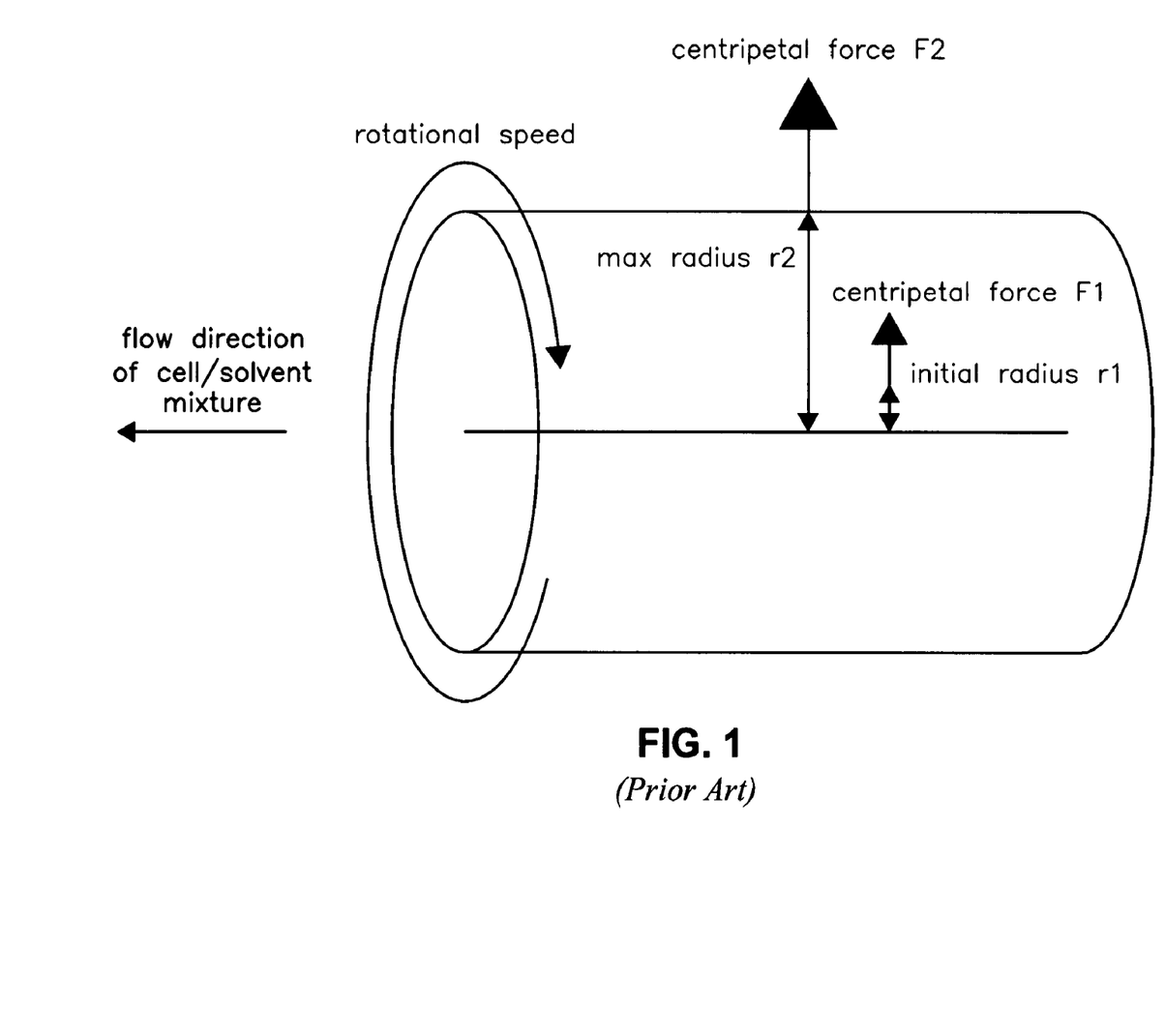
FIG. 1 illustrates centripetal forces acting on a specimen in a microcentrifuge.

Referring now to FIG. 1, centripetal forces acting on a specimen in a microcentrifuge are shown. Centripetal forces F1, F2 are shown for an initial radius r1 and a maximum radius r2 respectively. Generally, centripetal acceleration a is defined by the equation:

$$a = \frac{v^2}{r} = \frac{(2\pi r \omega)^2}{r} = 4\pi^2 \omega^2 r,$$

where r is the radius, and $\Omega$ is the rotational speed. The centripetal force is defined by the well-known relationship F=ma. Thus, if the product $\Omega^2 r$ is maintained, the centripetal forces acting on any specimen are the same for a standard centrifuge and a drum centrifuge.

In general, the centrifuging process of the invention allows specimen particles, such as biological cells, to be separated from debris according to size and density. Following the process of the invention as detailed below, it has been found experimentally that cells may advantageously be adequately centrifuged into a thixotropic optical gel, having a nominal viscosity of 10,600 poises, at 1000 rpm with a spin radius of 200 mm, yielding a product $\Omega^2 r = 200 \times 10^6$ [rpm$^2$][mm]. As an illustrative example, an equivalent centripetal acceleration can be achieved for a 2 mm radius if the rotational speed is 10,000 rpm. Rotational speeds up to 14,000 rpm are easily achieved with electric motor-based centrifuges. Higher rotational speeds can be generated with turbine-style motors, in some instances air pressure has been used to actuate these turbine-based rotation mechanisms.

Figure 2A:
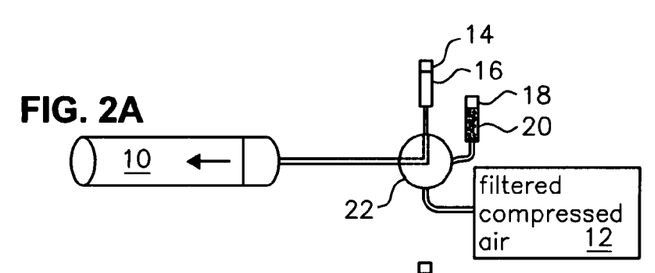
FIG. 2A–FIG. 2D schematically illustrate a drum centrifuge process for separation of specimen particles in accordance with the principles of the present invention.

Referring now to FIG. 2A–FIG. 2D, a procedure of how to use a drum centrifuge for separation of specimen particles, such as biological cells, in accordance with the teachings of the present invention is schematically illustrated. Referring now specifically to FIG. 2A, there shown is a drum centrifuge 10, a source of filtered compressed air 12, a mixture container 18 holding a specimen mixture 20, and a first selector valve 22. A gel container 14 holding optical gel 16 is included for embedding particles in gel. The first selector valve 22 is coupled to the source of filtered compressed air 12, the mixture container 18, and the gel container 14. The first selector valve 22 operates to selectively allow flows of optical gel, specimen mixture and filtered compressed air into the drum centrifuge 10 as the case may be.

The specimen mixture 20 may be any mixture including specimen particles to be prepared for analysis, especially, for example, a biological sample including a solvent and cell mixture where the cells are to be analyzed by automated or manual optical systems. One such system is described in pending U.S. patent application Ser. No. 10/716,744 to Fauver entitled "METHOD AND APPARATUS OF SHADOWGRAM FORMATION FOR OPTICAL TOMOGRAPHY," and published on Apr. 22, 2004 as publication number US-2004-0076319-A1. The disclosure of the patent application in publication number US-2004-0076319-A1 is incorporated herein by reference.

Figure 2B:
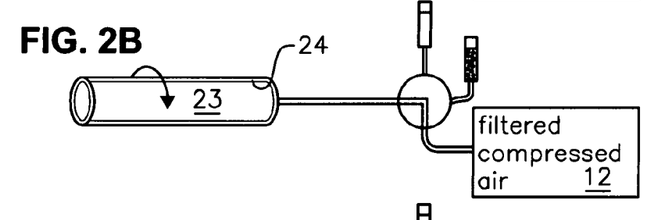

Referring now to FIG. 2B, after injecting a small quantity of optical gel 16 into the drum centrifuge 10, the optical gel 16 is centrifugated using a (not shown) motor as indicated by rotational arrow 23 to produce a uniform thin coating 24 on the inner wall of the drum centrifuge 10. The coating thickness may range, for example, from 100 microns to 1 mm, depending on inner diameter of drum centrifuge 10.

A gel, such as Nye OC431A optical gel or equivalent optical gels, may advantageously be used for embedding cells. The gel lines the wall of the drum centrifuge so that the cells adhere to the gel where they strike the gel-coated inner surface. Such optical gels may advantageously comprise commercially available index matching materials. The preferred gel index of refraction is the index of the mating materials during subsequent viewing or imaging. If the gel is used between two dissimilar materials, the preferred gel index is usually equal to the geometric mean of the indices of the two materials. Thixotropic gels are very useful for the purpose of embedding the particles in a film as a result of centrifugation. This allows the separation based on size and density to be maintained during flow of the specimen mixture 20. Commercial sources of optical gel include Nye Optical Gels, Dymax Corp, and Cargille Labs.

Figure 2C:
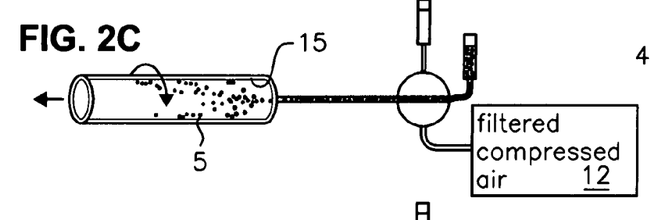

Referring now to FIG. 2C, the specimen mixture 20 is made to flow through the drum centrifuge 10 along its axis 11 while being rotated. Specimen particles 5, such as cells, from the specimen mixture 20 are accelerated toward the inner wall 15 of the drum centrifuge 10, with the smallest, lowest mass particles taking the longest time to reach the inner wall 15. The time taken to reach the inner wall 15 determines where along the axis 11 of the centrifuge that a particular particle will be embedded into the thin layer of gel lining the wall.

The initial radial spread determines the starting centripetal acceleration, though even cells exactly on axis of the centrifuge are unlikely to stay there since the only restoring forces acting on these cells are hydrodynamic focusing forces. Hydrodynamic focusing forces may advantageously be altered as desired by changing flow rate. Once a cell starts to move off axis, it will be increasingly accelerated toward the wall of the drum centrifuge due to an inherent instability in the system. Flow rate has an upper limit due to the finite length of the tube used for centrifugation. The radial spread of the cells as they flow through the drum centrifuge determines the resolution of separation of specimens along the drum centrifuge wall, with the smaller radial spread leading to better separation resolution. Vortexing of the fluid in addition to the hydrodynamic focusing keeps cells or other particulates in the center of the drum centrifuge. The centripetal force acting on the particles forces them out toward the wall of the drum centrifuge and into the optical gel, where they are trapped. Laminar flow of the specimen mixture 20 must be maintained prior to injection into the drum centrifuge.

Figure 2D:
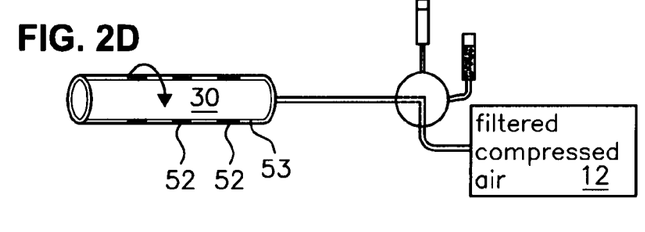

Referring now to FIG. 2D, after flow through of the specimen mixture 20 is complete, the drum centrifuge is flushed with filtered compressed air to accelerate removing solvent by evaporation. After the excess solvent is removed, a concentrated film 30 of particles, cells, for example, adhere to the inner wall 15. If optical gel has been added the concentrated film 30 will also include optical gel. If necessary, the concentrated film 30 may be centrifugated after the drum centrifuge is flushed to remove excess solvent and trapped bubbles. Specimen particles embedded in the concentrated film 30 register onto the inner wall 15 so as to form sections containing specimen particles 52 and sections with sparse or negligible specimen particles 53.

In one useful embodiment, the cells may advantageously be injected slightly off the drum centrifuge axis to ensure that a minimum centripetal acceleration is experience by all cells from the start of injection. If necessary, the specimen mixture 20 may advantageously be recycled through the drum centrifuge to increase the chances of particles being centrifuged into the gel. Alternatively, a fresh specimen mixture may be injected before removing the specimen deposit. If the solvent isn't immediately evaporated, it is air blown after the flow-through cycle is completed. The subsequent airflow helps to remove solvent from the gel by evaporation.

Figure 3A:
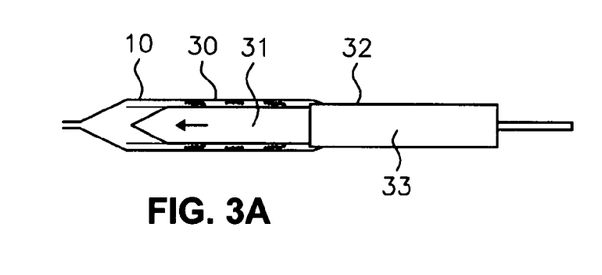
FIG. 3A and FIG. 3B schematically illustrate a plunger mechanism used to eject a gel containing specimen particles into a microcapillary tube for later selection and imaging as used in one embodiment of the invention.
Figure 3B:
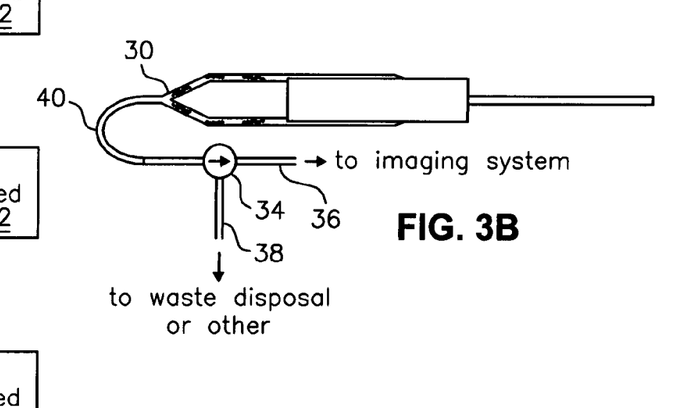

Referring now jointly to FIG. 3A and FIG. 3B, a schematic of a plunger mechanism 32 used to eject the concentrated film 30 of optical gel and specimen particles into a microcapillary tube 40 for later selection and imaging as used in one embodiment of the invention is shown. A second selector valve 34 may advantageously be used to select a desired section of the film 30 while rejecting others. The plunger mechanism 32 has two sections including a plunger tip 31 and a base 33. The plunger tip 31 advantageously has a diameter matched to that of the inner diameter of the film 30, so that the film 30 is not actuated by the plunger tip 31, but so that there is very little gap left between the film 30 and the plunger tip 31. The plunger base 33 has its diameter matched to that of the inner diameter of the drum centrifuge 10, so that the film 30 is forced forward. The plunger tip 31 maintains the registration of the specimen particles 5 during plunging. In this way the separation order is maintained, and specimens of interest may advantageously be conveniently injected into a microcapillary tube for imaging by a second selector valve 34 used to select which components are sent to an imaging system 48 and which are sent to waste disposal or other processing 42. Preferably, in operation, the sections containing specimen particles 52 will be sent to the imaging system, while the sections with sparse or negligible specimen particles 53 will be routed for disposal or other processing.

Figure 4A:
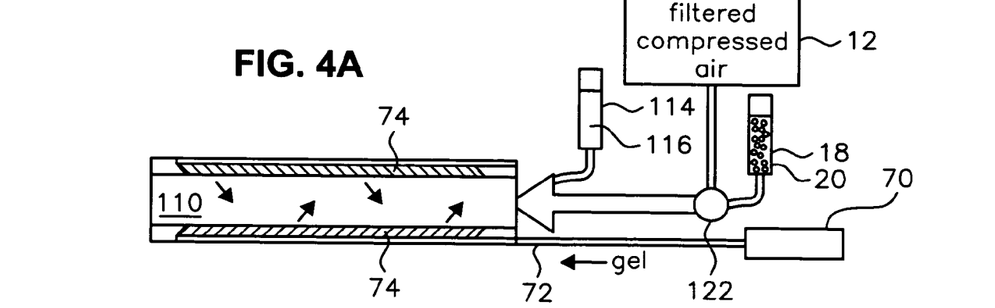
FIG. 4A–FIG. 4D schematically illustrate a process for separation of specimen particles using recessed wells in accordance with the principles of the present invention.

Referring now to FIG. 4A–FIG. 4D, there illustrated is a schematic for a drum centrifuge having recessed wells for separation of cells in accordance with the teachings of the present invention. Note that materials used are consistent with those described hereinabove with reference to FIG. 2A–FIG. 2D. Referring now specifically to FIG. 4A, there shown is a drum centrifuge 110 with recessed wells 74, a source of filtered compressed air 12, a mixture container 18 holding a specimen mixture 20, a selector valve 122 and a solvent container 114 holding solvent 116. The selector valve 122 is coupled to the source of filtered compressed air 12 and the mixture container 18. The selector valve 122 operates to selectively allow flows of specimen mixture and filtered compressed air into the drum centrifuge 110 as the case may be. A syringe pump 70 is connected to the recessed wells 74 by connecter 72. The syringe pump 70 operates to inject gel through connecter 72 into the recessed wells 74.

Figure 4B:
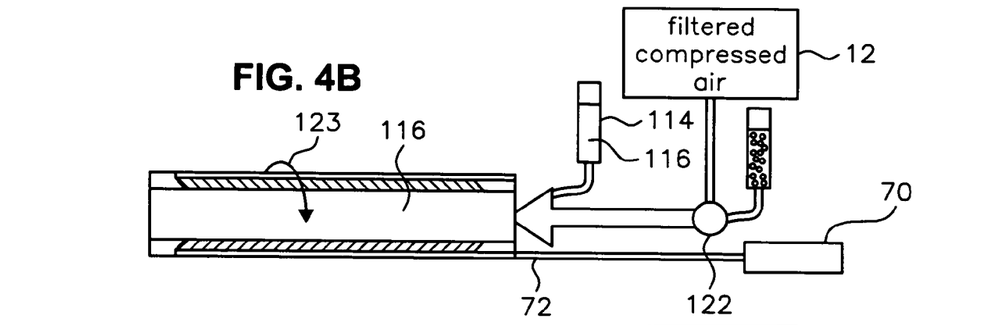

Referring now to FIG. 4B, after injecting a solvent 116 into the drum centrifuge 110, the solvent 116 is centrifugated using a (not shown) motor as indicated by rotational arrow 123. The centrifugation continues through the next step in the process.

Figure 4C:
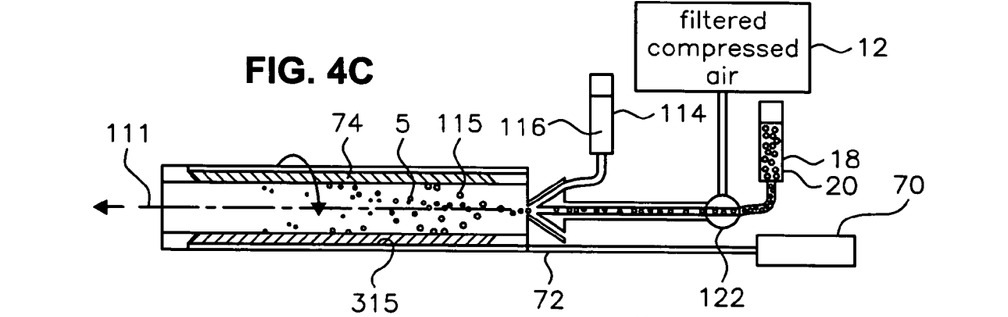

Referring now to FIG. 4C, the specimen mixture 20 is made to flow through the drum centrifuge 110 along its axis 111 while being rotated. Specimen particles 5, such as cells 115, from the specimen mixture 20 are accelerated toward the inner wall 315 of the drum centrifuge 10, with the smallest, lowest mass particles taking the longest time to reach the inner wall 315. The time taken to reach the inner wall 315 determines where along the axis 11 of the centrifuge that a particular particle will adhere to the wall or be embedded into the thin layer of gel in the recessed wells 74 lining the wall 315, as the case may be.

Figure 4D:
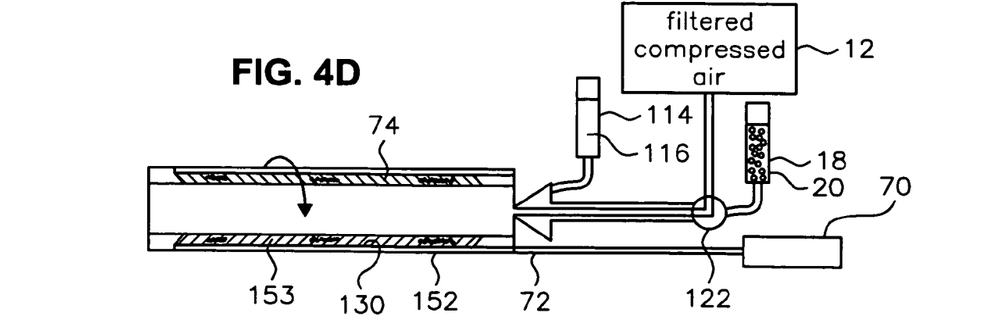

Referring now to FIG. 4D, after flow through of the specimen mixture 20 is complete, the drum centrifuge is flushed with filtered compressed air to help remove solvent by evaporation. When the excess solvent is removed a film 130 of particles, as for example, cells, and optical gel remains in the recessed wells 74. If necessary, the film 130 may be centrifugated after the drum centrifuge is flushed to remove excess solvent and trapped bubbles from the film 130. Note that, due to the operation of the centrifuge drum 110 specimen particles are separated into the film 130, wherein the specimen particles 5 register onto the inner wall 315 so as to form sections containing specimen particles 152 and sections with sparse or negligible specimen particles 153.

Figure 5A:
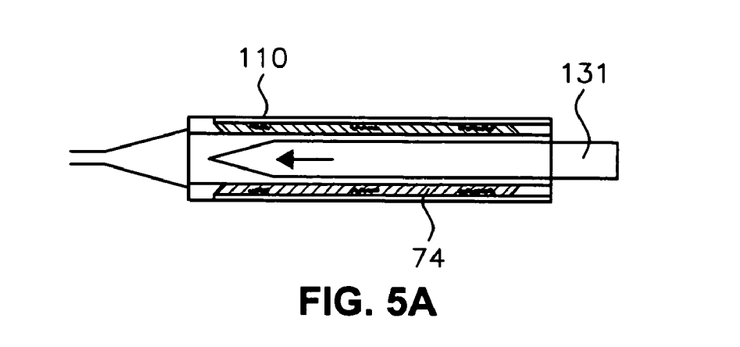
FIG. 5A–FIG. 5C schematically illustrate a plunger mechanism used to eject the gel containing specimen particles into a microcapillary tube for later selection and imaging as used in one embodiment of the invention.
Figure 5B:
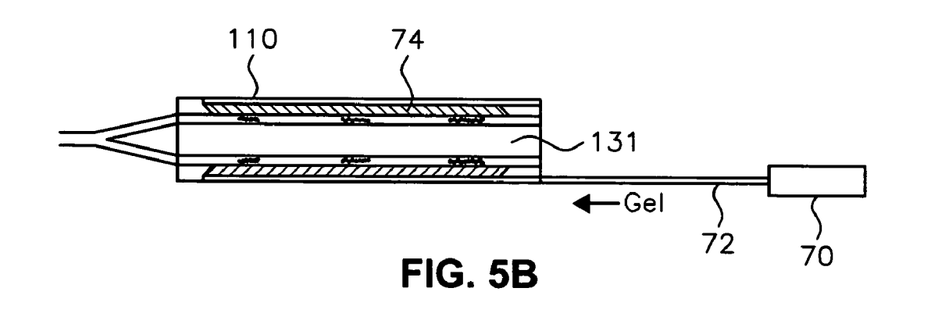
Figure 5C:
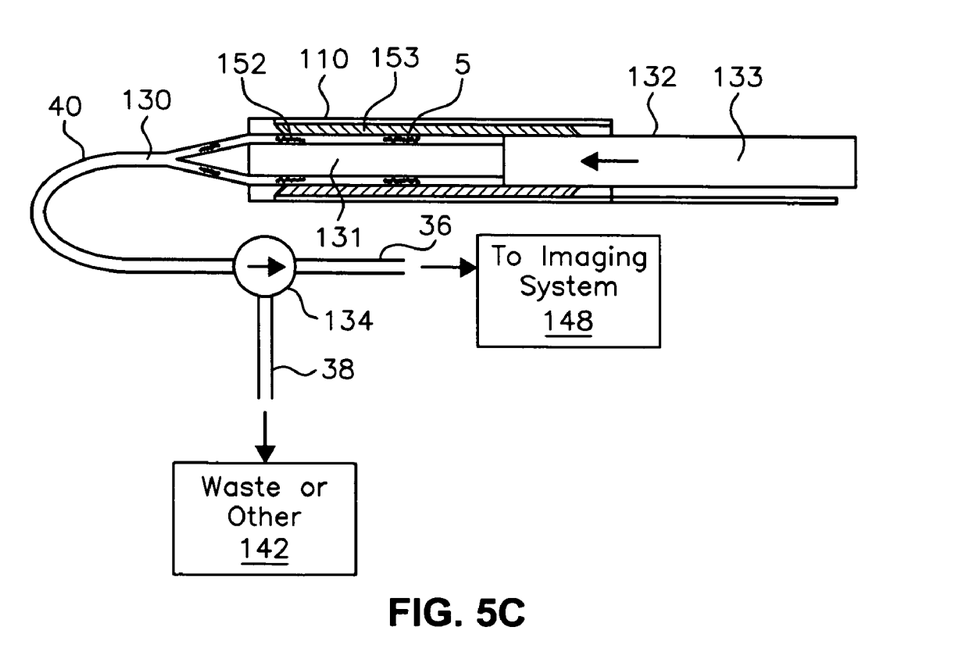

Referring now jointly to FIG. 5A, FIG. 5B and FIG. 5C a schematic of a plunger mechanism 132 used to eject the film 130 of optical gel and specimen particles into a microcapillary tube 40 for later selection and imaging as used in one embodiment of the invention is shown. A second selector valve 134 may advantageously be used to select a desired section of the film 130 while rejecting others. The plunger mechanism 132 has two sections including a plunger tip 131 and a base 133.

Actuation of the plunger tip 131 prevents rolling or mixing of the film 130 during ejection. The plunger tip 131 advantageously has a diameter matched to that of the inner diameter of the film 130, so that, when inserted, the plunger tip 131 does not actuate the film 130, but so that there is very little gap left between the film 130 and the plunger tip 131.

Referring particularly to FIG. 5C, there shown is a step in the process wherein a small volume of the film 130 including the sections containing specimen particles 152, is ejected from the recessed wells 74 onto the surface of the plunger tip 131. The plunger base 133 has its diameter matched to that of the inner diameter of the drum centrifuge 110, but smaller than the inner diameter of the recessed well portion of the drum centrifuge so that the film 130 is forced forward. The plunger tip 131 maintains the registration of the specimen particles 5 during plunging. In this way the separation order is maintained, and specimens of interest may advantageously be conveniently injected into a microcapillary tube for imaging by a second selector valve 134 used to select which components are sent to an imaging system 148 and which are sent to waste disposal or other processing 142. Preferably, in operation, the sections containing specimen particles 152 will be sent to the imaging system, while the sections with sparse or negligible specimen particles 153 will be routed for disposal or other processing.

Figure 5D:
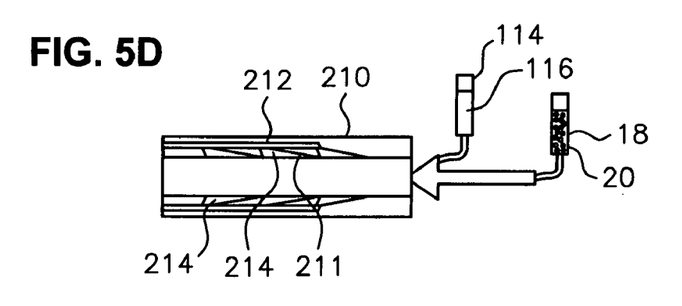
FIG. 5D–FIG. 5H, schematically illustrate an alternate embodiment for a drum centrifuge having recessed wells for separation of specimen particles without a trapping material in accordance with the teachings of the present invention.

Referring now to FIG. 5D–FIG. 5H, alternate embodiments for a drum centrifuge having recessed wells for separation of specimen particles without a trapping material in accordance with the teachings of the present invention are schematically illustrated. Note that materials used are consistent with those described hereinabove with reference to FIG. 2A–FIG. 2D. Referring now specifically to FIG. 5D, there shown is a drum centrifuge 210 with recessed particle trapping wells 214 having associated well valves 212, a mixture container 18 holding a specimen mixture 20, and a solvent container 114 holding solvent 116.

Figure 5E:
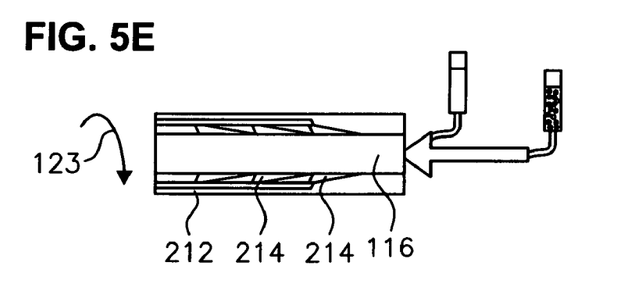

Referring now to FIG. 5E, a solvent 116 is injected into the drum centrifuge 210. The solvent 116 is centrifugated using a (not shown) motor as indicated by rotational arrow 123. The centrifugation continues through the next step in the process.

Figure 5F:
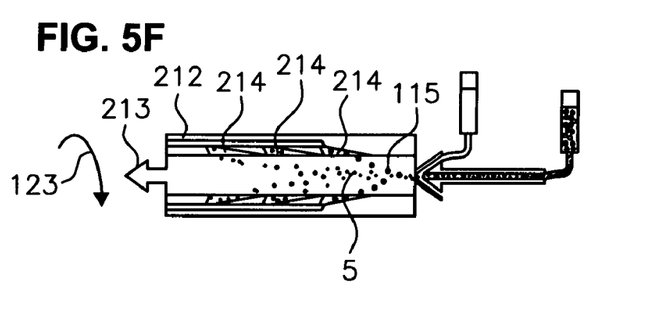

Referring now to FIG. 5F, the specimen mixture 20 is made to flow through the drum centrifuge 210 along its axis 213 while being rotated. Specimen particles 5, such as cells 115, from the specimen mixture 20 are accelerated toward an inner drum 211, with the smallest, lowest mass particles taking the longest time to reach the inner drum 211. In operation, the recessed particle trapping wells 214 in the surface of the inner drum 211 are used to catch specimen particles 5 as they sediment out of the flow stream. As in the configuration described with respect to FIG. 5A, specimen particles 5 are trapped in recessed particle trapping wells 214 at different positions along the drum axis depending on their size and density. The centrifugal force acting on the specimen particles 5 serves to concentrate them in each well, with each well itself acting like a small centrifuge tube.

Figure 5G:
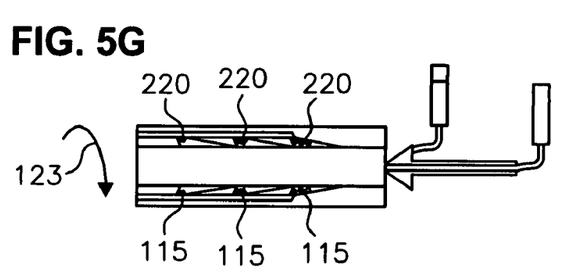

Referring now to FIG. 5G, each of the particle trapping wells 214 is angled so that force vectors due to flow and centrifugal force cause the particles to localize near its associated well valve 212. The associated well valve 212 at the apex 220 of the well that is the point of localization of particles, is closed for all steps until the specimen mixture 20 is depleted, or when the wells are full of particles.

Figure 5H:
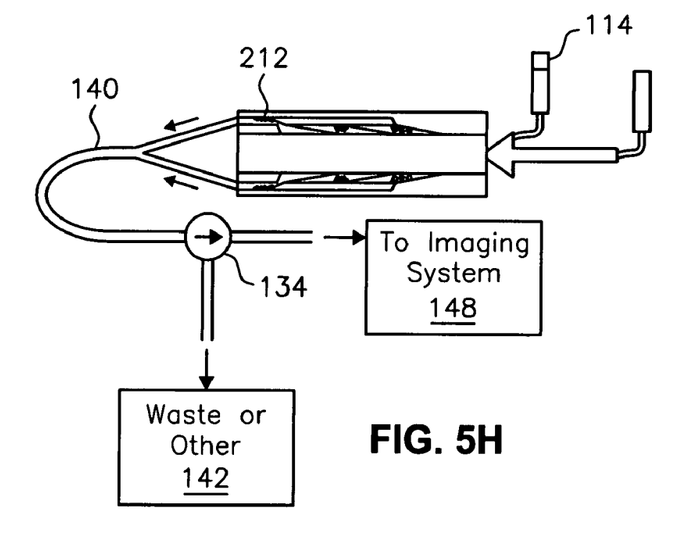

Referring now to FIG. 5H, at this point the associated well valve 212 is opened and, either additional flow of solvent, or continued centrifugal force, or both operate to redirect the particles out of the well once their associated well valves are opened. Separate pathways for each well may be provided, or all wells may lead to a common tube 140 for the particles to exit the drum centrifuge. Actuation of the associated well valves 212 in sequence allows particle flow with separation based on the grouping of said particles according to size and density. The stream of particles exiting the drum centrifuge may advantageously be subsequently disposed of 142 or directed for analysis 248.

Referring now to FIG. 9 and FIG. 9A–FIG. 9C, there illustrated are further alternate embodiments for a drum centrifuge having recessed wells for separation of specimen particles without a tapping material in accordance with the teachings of the present invention. Note that materials used and the operational processes of the drum centrifuge and recessed wells are consistent with those described hereinabove with reference to FIG. 5D–FIG. 5H, except as specifically noted below. Refining now specifically to FIG. 9, there shown is a drum centrifuge 310 with an inner drum 311 including at least one recessed particle trapping well 314 having at least one associated well valve 313, a mixture container 18 holding a specimen mixture 20, and a solvent container 114 holding solvent 116.

As in the configuration described with respect to FIG. 5A, specimen particles are trapped in recessed particle trapping wells 314 at different positions along the drum axis depending on their size and density. The centrifugal forces, F (as shown in FIG. 9A–FIG. 9C) acting on the specimen particles serve to concentrate them in each well, with each well itself acting like a small centrifuge tube.

Figure 9:
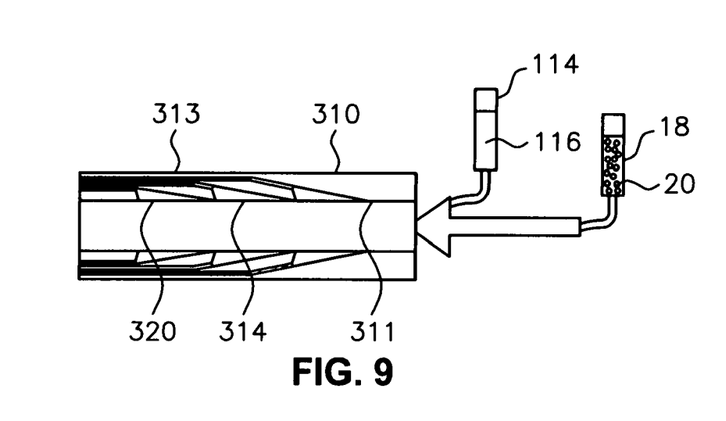
FIG. 9 and FIG. 9A–FIG. 9C schematically illustrate further ultimate embodiments for a drum centrifuge having recessed wells for separation of specimen particles without a trapping material in accordance with the teachings of the present invention.
Figure 9A:
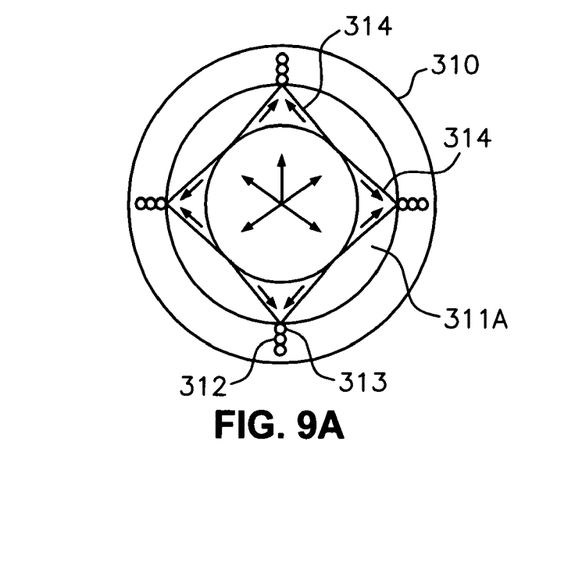
Figures 9B, 9C:
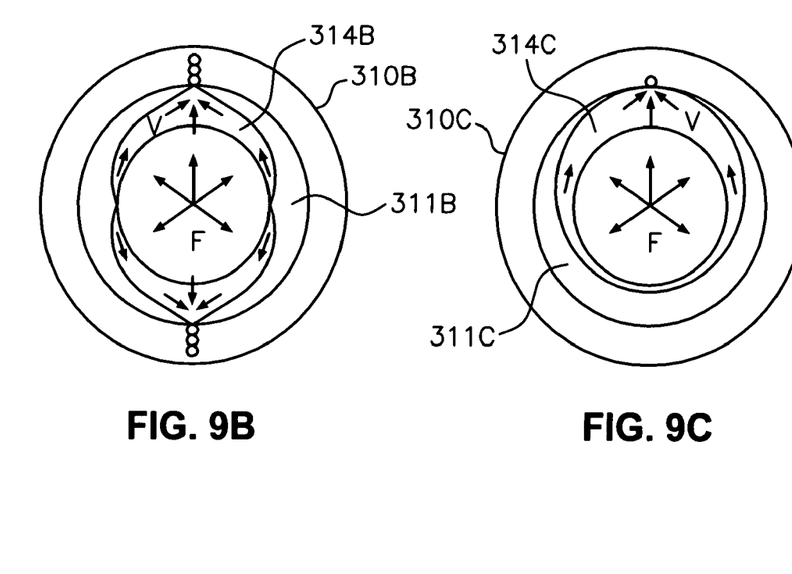

Referring now to FIG. 9A, an enlarged crossectional end view of an embodiment of the drum centrifuge 310 of FIG. 9 is shown. Each of the particle trapping wells 314 is angled so that force vectors, V, due to flow and centrifugal force cause the particles to localize near its associated well valve 313. The associated well valve 313 at the apex of the well that is the point of localization of particles, is closed for all steps until the specimen mixture 20 is depleted, or when the wells are full of particles. The associated well valve 313 is opened and, either additional flow of solvent, or continued centrifugal force, or both operate to redirect the particles out of the well once. Separate pathways 312 for each well may be provided, or all wells may lead to a common tube for the particles to exit the drum centrifuge (as best shown in FIG. 5D). Actuation of the associated well valves 313 in sequence allows particle flow with separation based on the grouping of said particles according to size and density. While the number of particle trapping wells 314 may vary both along the length and around the circumference of the drum centrifuge 310. The plurality of wells may advantageously comprise four wells evenly spaced around the circumference of the drum centrifuge 310 at a location 320 along the length of the drum centrifuge 310. In another embodiment as shown in FIG. 9B, the at least one well may advantageously comprise two wells 314B included in inner drum 311B, wherein the wells are evenly spaced around the circumference of the drum centrifuge 310B. Yet another embodiment comprises a single well 314C in inner drum 311C as shown in FIG. 9C at a location 320 along the length of the drum centrifuge 310C.

Figure 6A:
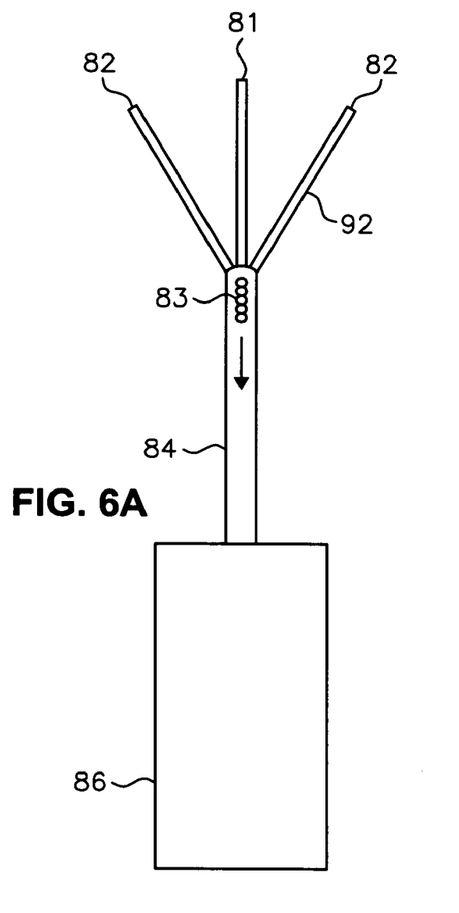
FIG. 6A–FIG. 6C schematically illustrate a system for using hydrodynamic focusing for centering specimen particles in a cylinder.
Figure 6B:
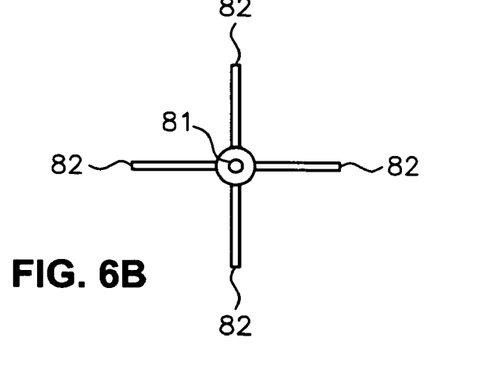

Referring now jointly to FIG. 6A and FIG. 6B, there schematically illustrated is a front view and end view respectively of a system for using hydrodynamic focusing for centering specimen particles in a cylinder. After concentration of specimen particles in the desired medium, such as a solvent, using the centrifugation methods described hereinabove, a high concentration (e.g. approximately 50% specimen particles by volume) of a cell-medium mixture 81 is injected into a flow tube 84. A second medium 82 is injected to form a focusing flow stream as, for example, by injecting into four or more ports 92. The second medium 82 advantageously comprises a medium, such as a solvent, without specimen particles. At least two pairs of opposing flow streams of the second medium 82 serve to focus and center the cell-medium mixture 81 along two orthogonal axes, resulting in specimen particles 83 centered within the microcapillary flow tube 84. Alternatively, the focusing flow stream may be a focused annular ring of solvent flow around the cell/solvent mixture.

Ideally, laminar flow without rippling is achieved for hydrodynamic focusing (Reynolds number Re<4 to 25 [See Transport Phenomena by Bird, Stewart, Lightfoot. John Wiley & Sons 1960]) in accordance with the relationship, $$Re = \frac{\rho \langle v \rangle D}{\mu},$$

where $\rho$ is density, $\langle v \rangle$ is average (characteristic) flow velocity, D is characteristic length and $\mu$ is (absolute) viscosity. In the case of a circular cross-section tube, the characteristic length D is the inner diameter of the microcapillary flow tube 84.

Figure 6C:
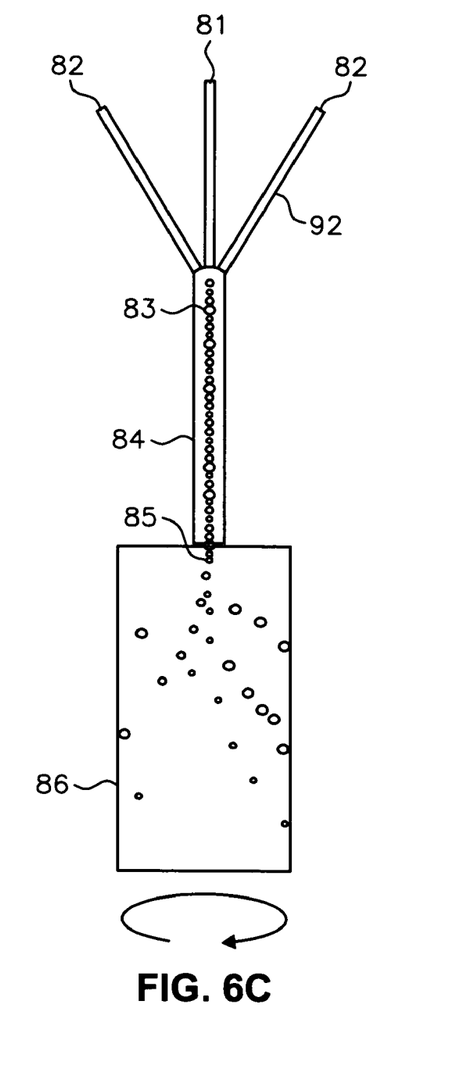

Referring now to FIG. 6C, a side view of the system for using hydrodynamic focusing for centering specimen particles in cylindrically-shaped medium as shown in FIG. 6A is schematically illustrated. Once the cell concentration has been increased, the cell-medium mixture 81 is injected substantially simultaneously with the four or more flow streams of medium 82 at a constant rate. Specimen particles 81 in solvent, typically xylene, are injected simultaneously with pure solvent 82 to produce a focusing of specimen particles prior to injection in the drum centrifuge. The focused cell-solvent stream 83 flows through tube 84 until it enters the drum centrifuge 86 where the cell stream is no longer confined as shown at point 85 by the smaller diameter of tube 84. Producing a tightly focused cell-solvent stream at point 85 reduces errors in separation of specimen particles based on size and density.

Figure 7:
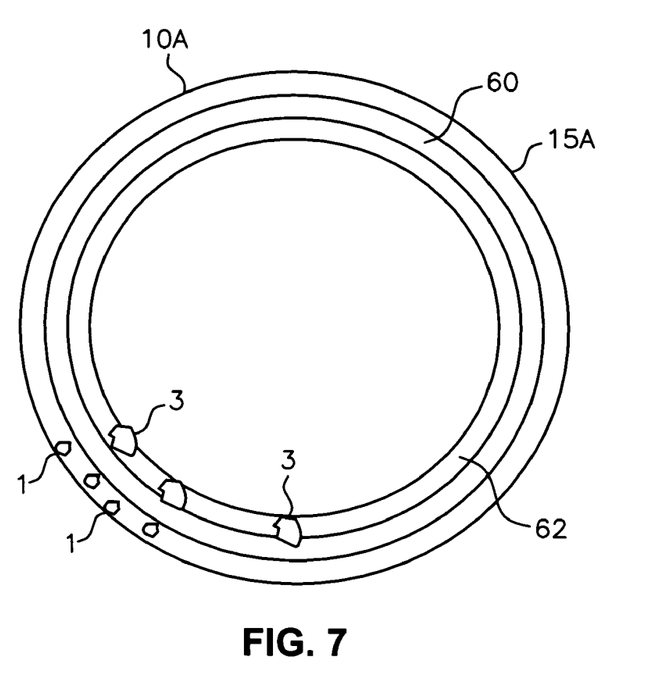
FIG. 7 schematically illustrates a cross-sectional view of an alternative embodiment of a drum centrifuge constructed in accordance with the present invention including a drum centrifuge with filters.

Referring now to FIG. 7, a cross-sectional view of an alternative embodiment of a drum centrifuge constructed in accordance with the present invention including a drum centrifuge with filters is schematically illustrated. A drum centrifuge 10A includes an inner wall 15A, a first filter 60 and a second filter 62. The first filter 60 may advantageously comprise a membrane of sufficiently sized filter pores to pass both particles of no interest 3 and particles of interest 1. The second filter 62 may advantageously comprise a membrane of smaller sized filter pores to trap particles of no interest 3 and pass particles of interest 1. Thus, when the tube is rotated particles of interest are forced to the inner wall 15A. The particles of interest can then be recovered by removing the filters and subsequently flushing the drum centrifuge 10A or mechanically recovering the particles of interest 1.

Figure 8:
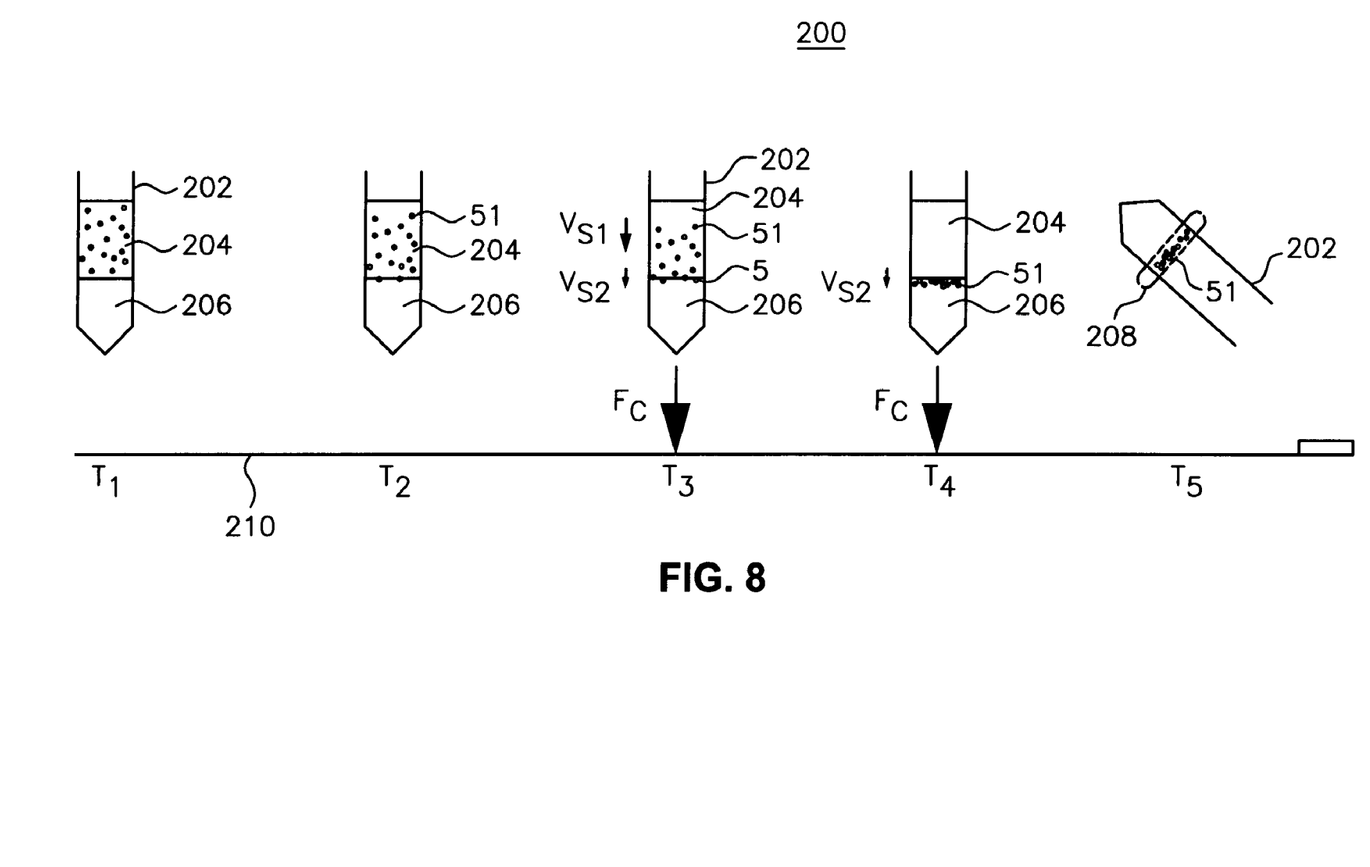
FIG. 8 schematically illustrates a process flow diagram of an alternative embodiment of a method for concentration of specimen particles in accordance with the present invention.

Now referring to FIG. 8, a process flow diagram of an alternative embodiment of a method for concentration of cells in accordance with the present invention is schematically illustrated. For illustrative purposes, the process is described as proceeding along a relative time line 210. At step $T_1$ a tube 202 has a bottom section filled with a high viscosity substance 206. The tube 202 also has an upper section with cells 51 in suspension in low viscosity supernatant 204, which has a density less than the cells. The high viscosity substance 206 may advantageously have a density slightly less than or equal to the density of the cells 51. For example, the high viscosity substance may comprise a thixotropic gel and further, the gel may have a viscosity greater than about 100000 cps. The low viscosity supernatant 204 may advantageously comprise a solvent, such as, for example, xylene or an equivalent substance.

At step $T_2$ cells 51 begin to sediment out of the low viscosity supernatant 204 into the high viscosity substance 206 due to gravitational forces. At step $T_3$, a centrifugal force $F_c$ is applied to produce acceleration which produces a drag-limited velocity of the cells in the direction of the high viscosity substance 206. The sedimentation rate in the low viscosity solvent is referenced as $V_{s1}$ and the sedimentation rate in the high viscosity substance is referenced as $V_{s2}$. The difference in sedimentation rates is determined by difference in viscosities of the two substances, and the density of the substances relative to that of the individual cells. The centrifugal force $F_c$ is applied until, at step T4, substantially all of the cells 51 are embedded in the high viscosity substance 206. At step $T_5$, the low viscosity supernatant 204 is removed, leaving a layer of high cell concentration 208 embedded in the high viscosity substance 206.

The concentration of the cells, or other specimen particles, where the high viscosity substance 206 comprises a medium that is suitable for optical imaging provides advantages in addition to aiding optical imaging. For example, the high viscosity substance helps to prevent biofouling because the cells are encapsulated and have little exposure to the inner surface of a tube, such as a glass microcapillary tube, to which they could adhere. The use of a high viscosity substance 206 also facilitates extraction of cells from a container with very low loss of cells. This is an advantage over other practices where cells are concentrated in a pellet by centrifugation, causing retention of some solvent with the pellet, or where the cells stick to the inside of a centrifuge tube and are difficult, if not impossible, to recover.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, devices and algorithms, and that various modifications, both as to the equipment details and operating procedures, may be accomplished without departing from the true spirit and scope of the present invention.

What is claimed is:

1. A process for separation of specimen particles, the process comprising coating a cylinder having an inner wall and a cylinder axis with an optical gel coating on the inner wall by injecting an optical gel into the cylinder and centrifuqating the optical gel to produce a uniform coating of the optical gel on the inner wall, then flowing a specimen mixture including solvent through the cylinder while the cylinder is being continuously rotated, wherein the specimen mixture is initially directed to flow along the cylinder axis and such that specimen particles from the specimen mixture are accelerated off the cylinder axis toward the inner wall, so as to form a film of specimen particles embedded into the uniform coating of the optical gel, and ejecting the film of specimen particles embedded into the uniform coating of the optical gel using a plunger mechanism having a tip and a base where the tip has a diameter matched to that of the inner diameter of the film of biological cell specimen particles embedded into the gel, so that the film of specimen particles embedded into the uniform coating of the optical gel is not actuated by the plunger tip, but so that there is a gap left between the film of specimen particles embedded into the uniform coating of the optical gel and the plunger tip, and wherein the plunger base has its diameter matched to that of the inner diameter of the cylinder, so that the film of specimen particles embedded into the uniform coating of the optical gel is forced forward when the plunger mechanism base engages the inner wall of the cylinder.

2. The process of claim 1 further comprising the step of removing the solvent from the film of specimen particles embedded into the uniform coating of the optical gel.

3. The process of claim 1 wherein the film of specimen particles embedded into the uniform coating of the optical gel include specimens of interest in a separation order and wherein the plunger tip maintains the separation order during plunging.

4. The process of claim 1 further comprising the steps of injecting the film of specimen particles into a microcapillary tube and operating a selector valve to discard portions of the film of specimen particles having negligible specimen particles.

5. The process of claim 1 wherein the uniform coating of the optical gel has a thickness that ranges from 100 microns to 1 mm.

6. The process of claim 1 including the step of blowing compressed air through the cylinder to remove solvent before ejecting the film of specimen particles embedded into the uniform coating of the optical gel.

7. The process of claim 1 wherein the specimen mixture comprises a biological sample including a solvent and cell mixture.

8. A process for separation of specimen particles, the process comprising the steps of:
    injecting optical gel into a centrifuge having an inner wall;
    centrifuging the optical gel to produce a coating of optical gel on the inner wall;
    flowing a specimen mixture including solvent through the centrifuge while the centrifuge is rotated such that specimen particles from the specimen mixture are accelerated toward the inner wall and embedded into the coating of optical gel;
    removing solvent from the coating of optical gel and specimen particles to form a film of specimen particles in optical gel; and
    ejecting the film of specimen particles in optical gel into a microcapillary tube by using a plunger mechanism having a tip and a base where the tip has a diameter matched to that of the inner diameter of the film of specimen particles in optical gel, so that the film of specimen particles in optical gel is not actuated by the plunger tip, but so that there is a gap left between the coating and the plunger tip, and wherein the plunger base is matched to engage the inner wall, so that the film of specimen particles in optical gel is forced forward when the base engages the inner wall of the centrifuge.

9. The process of claim 8 wherein the optical gel is selected from the group consisting of optical gels, oils, fluids, polymer and epoxy.

10. The process of claim 8 further comprising the step of operating a selector valve to discard portions of the film of specimen particles in optical gel having negligible specimen particles.

11. The process of claim 8 wherein the film of specimen particles in optical gel includes specimens of interest in a separation order and wherein the plunger tip maintains the separation order during plunging.

12. The process of claim 8 wherein the coating has a thickness that ranges from 100 microns to 1 mm.

13. The process of claim 8 wherein the specimen mixture comprises a biological sample including a solvent and cell mixture.

14. A process for separation of specimen particles, the process comprising the steps of:
    coating a cylinder having an inner wall and a cylinder axis by injecting an optical gel into the cylinder and centrifugating the optical gel to produce a uniform coating of the optical gel on the inner wall, wherein the optical gel has a selected index of refraction matched for subsequent imaging of the specimen particles;
    flowing a specimen mixture including solvent through the cylinder while the cylinder is being continuously rotated, wherein the specimen mixture is initially directed to flow along the cylinder axis and such that specimen particles from the specimen mixture are accelerated off the cylinder axis toward the inner wall, so as to form a film of specimen particles embedded into the uniform coating of the optical gel; and
    ejecting the film of specimen particles embedded into the uniform coating of the optical gel from the cylinder into a microcapillary tube for imaging by an imaging system.

15. A flow-through centrifuge system comprising:
a centrifuge having a gel-coated inner surface;
a mixture container for holding a specimen mixture coupled to the centrifuge, wherein the specimen mixture is injected into the centrifuge and rotated to embed specimen particles into the gel-coated inner surface of the centrifuge to form a film of gel and specimen particles; and
a plunger mechanism having a tip and a base where the tip is sized so that there is a gap left between the film of gel and specimen particles and the tip when the tip is inserted into the centrifuge, and wherein the base is sized so that the film of gel and specimen particles is forced forward when the base engages the inner surface of the centrifuge.

16. The flow through centrifuge system of claim 15 further comprising:

a microcapillary tube coupled to receive the film of gel and specimen particles; and a selector valve for selecting a section of the film of gel and specimen particles.

17. The system of claim 15 wherein the specimen mixture comprises a biological sample including a solvent and cell mixture.

* * * * *

UNITED STATES PATENT AND TRADEMARK OFFICE
CERTIFICATE OF CORRECTION

PATENT NO. : 6,991,738 B1  
APPLICATION NO. : 10/964513  
DATED : January 31, 2006  
INVENTOR(S) : Fauver et al.

It is certified that error appears in the above-identified patent and that said Letters Patent is hereby corrected as shown below:

Column 9, lines 20 and 21 Replace "centrifuqating" with --centrifugating--.

Signed and Sealed this

Ninth Day of January, 2007

JON W. DUDAS  
*Director of the United States Patent and Trademark Office*